US009091662B1

(12) United States Patent
Maddock et al.

(10) Patent No.: US 9,091,662 B1
(45) Date of Patent: Jul. 28, 2015

(54) SYSTEM AND METHOD FOR AUTOMATIC CAMERA CALIBRATION AND ALIGNMENT DETERMINATION

(75) Inventors: Timothy M. Maddock, Hendersonville, NC (US); Joseph P. Maddock, Hendersonville, NC (US)

(73) Assignee: Cognex Corporation, Natick, MA (US)

( * ) Notice: Subject to any disclaimer, the term of this patent is extended or adjusted under 35 U.S.C. 154(b) by 596 days.

(21) Appl. No.: 12/644,174

(22) Filed: Dec. 22, 2009

(51) Int. Cl.
*H04N 7/18* (2006.01)
*G01N 21/88* (2006.01)

(52) U.S. Cl.
CPC .......... *G01N 21/8806* (2013.01); *H04N 7/183* (2013.01)

(58) Field of Classification Search
None
See application file for complete search history.

(56) References Cited

U.S. PATENT DOCUMENTS

| | | | |
|---|---|---|---|
| 6,101,455 A | 8/2000 | Davis | |
| 6,301,396 B1 | 10/2001 | Michael et al. | |
| 6,442,291 B1 * | 8/2002 | Whitman | 382/141 |
| 6,648,730 B1 | 11/2003 | Chokshi et al. | |
| 6,757,629 B2 | 6/2004 | Takizawa et al. | |
| 6,809,330 B2 | 10/2004 | Krohn et al. | |
| 7,233,841 B2 | 6/2007 | Sadighi et al. | |
| 7,542,821 B2 | 6/2009 | Floeder et al. | |
| 2005/0259158 A1 * | 11/2005 | Jacob et al. | 348/218.1 |
| 2008/0195343 A1 | 8/2008 | Osterlund et al. | |
| 2010/0110174 A1 * | 5/2010 | Leconte | 348/92 |

FOREIGN PATENT DOCUMENTS

WO     WO 9820445     5/1998

\* cited by examiner

*Primary Examiner* — Frederick Bailey
(74) *Attorney, Agent, or Firm* — Loginov & Associates, PLLC (57) ABSTRACT

This invention provides a system and method for automatic runtime determination of calibration and alignment of multiple cameras in a cross surface inspection arrangement. A plurality of flags each move into and out of a field of view of each of the cameras. These flags actuate at predetermined times. When actuated, the flags present a known geometric shape to the region of interest, which can be used to determine whether a camera has drifted in calibration or alignment with respect to a previously calibrated, trained image of the flags. The flags can be mounted on rotary actuators that are placed at predetermined intervals along an illumination bar. The illumination bar can be located on a side of a moving web opposite a side facing the cameras. The illumination bar projects a light line through the translucent web that is momentarily interrupted at periodic intervals by the actuated flags. In operation, the cameras operate a runtime inspection process. A validation controller signals each camera to cease a runtime inspection process and begin a validation process within the cameras. The flags move into a deployed orientation. While deployed, the validation application within the camera treats the flags as inspection defects and compares them to trained models. The system determines whether the cameras are within accepted parameters.

23 Claims, 6 Drawing Sheets

SYSTEM AND METHOD FOR AUTOMATIC CAMERA CALIBRATION AND ALIGNMENT DETERMINATION

FIELD OF THE INVENTION

This invention relates to the validation of machine vision camera system camera calibration and runtime operation.

BACKGROUND OF THE INVENTION

Machine vision is used in an increasing number of manufacturing operations. One role for machine vision (or a "vision system") is the verification of product quality through inspection. In a typical vision system inspection arrangement, one or more cameras are positioned over a moving line, with appropriate illumination, and images of the line, within the field of view of each camera are acquired and processed. The processing can include a comparison of the acquired image to a trained model using appropriate vision system applications (e.g. edge detection, blob analysis, rotation and scale-invariant search, etc.) that reside on a processor within the camera, or in an interconnected processor. The results of the processing can indicate when a defect is present. These results can be used by a controller to direct various operations, such as issuing alarms and alerts, stopping the moving line and actuating a part-reject mechanism.

Figure 1:
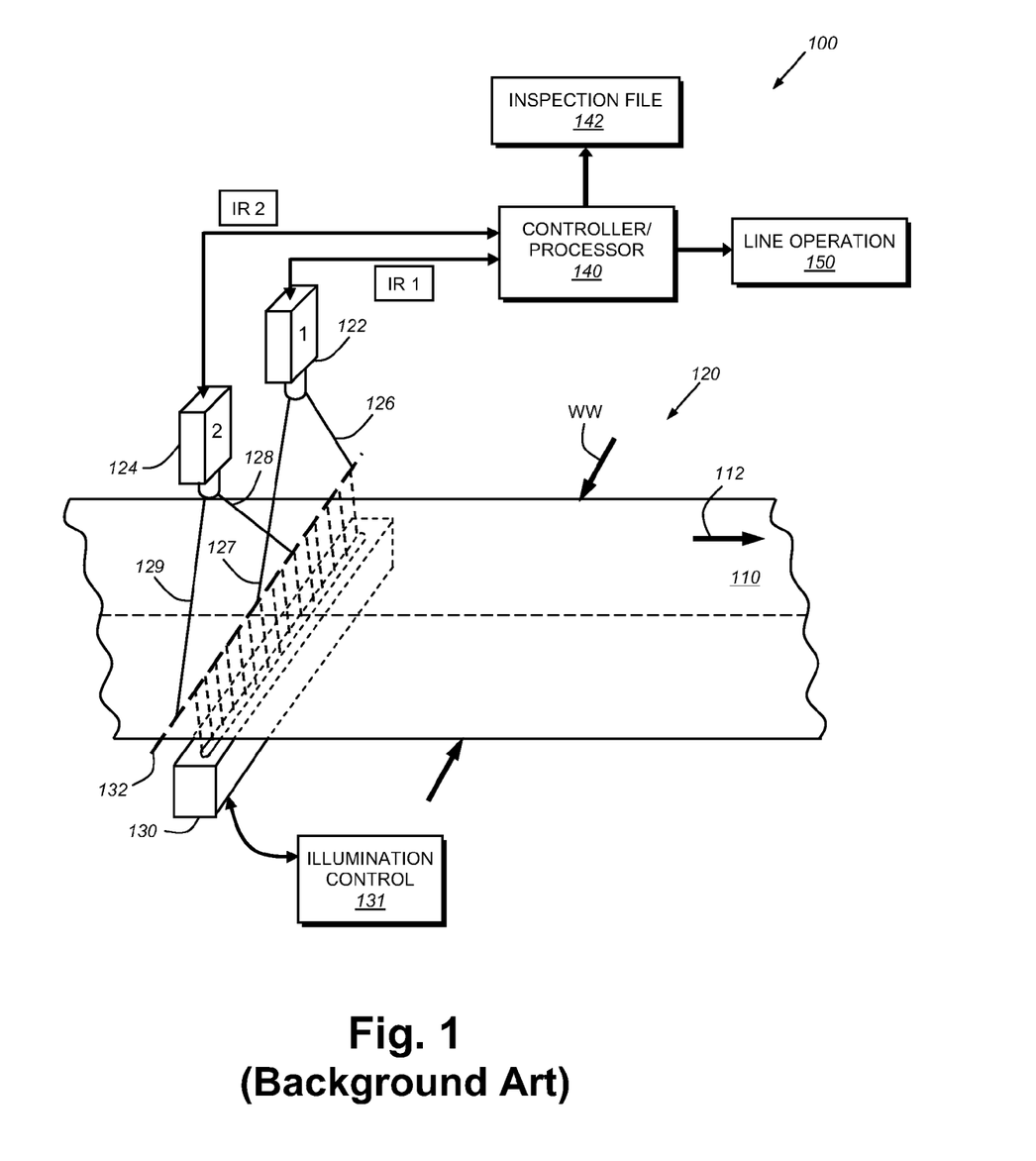
FIG. 1 is a schematic perspective view of an exemplary multi-camera, cross-web inspection system having an illuminator and associated controller according to a prior art implementation.

FIG. 1 shows a typical vision system inspection arrangement 100 used to inspect for defects on a moving web 110 or similar continuous moving surface. As the web 110 moves (arrow 112) downstream, it passes through at least one inspection station 120 containing at least two cameras Camera 1 (122) and Camera 2 (124). These cameras each define a respective field of view (lines 126, 127 and lines 128, 129) that together covers the entire width WW of the web 110. This can be termed a "cross-web" inspection system. In this example, each field of view overlaps (crossing lines 127, 128) to ensure full acquisition of the web line. The outer edges of the field of view (outer lines 126, 129) extend at least to the opposing edges of the web 110, or to edges of the desired inspection region. The cross-web field of view in this example is illuminated by a bar illuminator 130 that resides on a back side of the web (opposite the camera-facing web side) so as to generate an illumination line (dashed line 132) that projects translucently through the web. The illuminator can be an LED-based illuminator, and can be controlled by an appropriate controller 131. The cameras 122, 124 acquire a stream of images that include the region within the illumination line. Any defects occurring within the line are identified by the vision system application that (in this example) resides in each camera 122, 124. The inspection results IR1 and IR2 of each respective camera 122 and 124 for each image frame are transmitted to a controller and/or processor 140 that directs a desired line operation 150—for example issuing an alert and/or stopping the moving line. The results can also be placed in an inspection file (i.e. a computer-readable file) 142 that is appended to information regarding the web for quality control and other purposes.

The exemplary web inspection arrangement 100, and other surface inspection systems, may operate continuously for days without stoppage. One particular concern is that the system is functioning properly, if at all, after an extended period of runtime. That is, one or both cameras may be malfunctioning and allowing defects to pass undetected. A popular technique for determining continued operation of the inspection cameras is to insert an object, such as an operator's hand, briefly into the field of view of each camera. If the controller processor responds, detecting an obstruction, then the camera is at least nominally functioning.

A further concern is whether the camera system is still within acceptable calibration. Calibration of each camera occurs at setup time, and typically involves skilled technicians. Over time calibration can drift due to internal and external changes in the camera setup. For example vibration or a jar to a camera can cause it to misalign, and lose calibration. If the calibration is sufficiently drifted, then it is desirable to perform a recalibration of the camera system. Likewise, illumination intensity or focus may have diminished or changed in an unacceptable way over time. Due to the need to take the line out of service and the use of skilled technicians, recalibration is best performed when actually needed. Conversely, when recalibration is needed, it should be performed relatively soon so that inspection errors do not occur.

More generally, under various industry quality standards, such as ISO 9001, product quality and equipment performance must be monitored. The ability to regularly and continuously validate the alignment, focus and overall performance of cameras in an inspection system, without affecting the inspection results is a highly desirable and heretofore unachieved goal.

Accordingly, it is desirable to provide a system and method for allowing the state of vision system function to be determined in a surface inspection arrangement. The system and method should desirably allow the present calibration to be determined. Such determination should be performed during runtime without stopping the line or generally degrading ongoing inspection activities.

SUMMARY OF THE INVENTION

This invention overcomes disadvantages of the prior art by providing a system and method for automatic runtime determination of calibration and alignment of multiple cameras in a cross surface inspection arrangement. The system and method employs a plurality of movable flags or other structures that selectively move into and out of a field of view of each of the multiple cameras. These flags are operated at predetermined times, known to the inspection application of the system. When actuated, the flags present a known geometric shape to the region of interest, which can be used to determine whether a camera has drifted in calibration or alignment with respect to a previously calibrated, trained image of the flags. In an illustrative embodiment, the flags can be mounted on rotary actuators that are placed at predetermined intervals along an illumination bar. The illumination bar can be located on a side of a moving web opposite a side facing the cameras. The illumination bar projects a light line through the translucent web that is momentarily interrupted at periodic intervals by the actuated flags.

In operation, the cameras operate a runtime inspection process that can include creation of an inspection file containing the results of the inspection with any identified defects. At a predetermined time, a validation controller provides a signal to each camera to cease a runtime inspection process and begin a validation process within the cameras. The actuator controller then operates the flag actuators in response to the validation controller's signal and the flags move into a deployed orientation with respect to the region of interest (for example the illumination bar). While deployed, the validation application within the camera treats the flags as inspection defects and compares them to trained models. A validation file, similar to an inspection file is created. If the positioning, size, contrast, etc., of the validation flags do not conform sufficiently with the trained model parameters, then the system indicates an out-of-calibration condition. This can cause the issuance of an alert or other operation, and can be stored on the validation file with other validation results.

Illustratively, the inspection file and the validation file are each appended to information regarding the particular production run.

In an illustrative embodiment, a system for calibrating a plurality of vision system cameras arranged to provide cross-surface inspection results includes an illumination strip extending across the moving surface that provides a region of interest with respect to a moving surface for image acquisition by each of the plurality of vision system cameras. A runtime surface inspection application associated with each of the vision system cameras provides the inspection results. At least one flag within a field of view of each of the vision system cameras selectively actuates to occlude a portion the illumination strip at predetermined times. A validation application directs the at least one flag in each field of view of each vision system camera to actuate and validates acquired images of each at least one actuated flag with respect to an expected configuration of each at least one flag. The expected configuration can be based upon stored model data relating to at least one of an orientation, location, size and intensity of the at least one flag. A validation controller directs the validation application to start and a runtime surface inspection application to cease, and to actuate the at least one flag. The surface inspection application can include the validation application, and the expected configuration can be based upon a set of model data provided to the surface inspection application to provide validation results. The inspection results and the validation results can each provided in a respective file. The files can be associated with a predetermined production run, such as a web roll. The flags can be mounted on a rotary actuator, and each actuator can mounted on the illumination strip on a side of the surface opposite a side facing the plurality of vision system cameras. Moreover, the at least one flag includes a surface that is at least part translucent so as to provide reduced transmission of light from the illumination strip, and the validation application detects variations in the reduced transmission of light. The at least on flag and its actuation mechanism can be constructed in a variety of manners including, but not limited to a rotary actuator, a linear actuator and a solid state window section overlying the illuminator window or formed as part of the illuminator window. The solid state window can use, for example an LCD array to selectively occlude the illumination strip in an opaque, translucent or patterned manner.

In an illustrative embodiment, a corresponding method for calibrating a plurality of vision system cameras arranged to provide cross-surface inspection results includes illuminating a region of interest that extends across the moving surface. Runtime images are acquired with each of the plurality of vision system cameras. Surface inspection is performed with respect to each of the vision system cameras, so as to provide the inspection results. At least one flag is actuated within a field of view of each of the vision system cameras to occlude a portion the illuminated region of interest at predetermined times. The actuating of the at least one flag in each field of view of each vision system camera is directed and then acquired images of each at least one actuated flag are validated with respect to an expected configuration of each at least one actuated flag.

BRIEF DESCRIPTION OF THE DRAWINGS

The invention description below refers to the accompanying drawings, of which.

DETAILED DESCRIPTION

Figure 2:
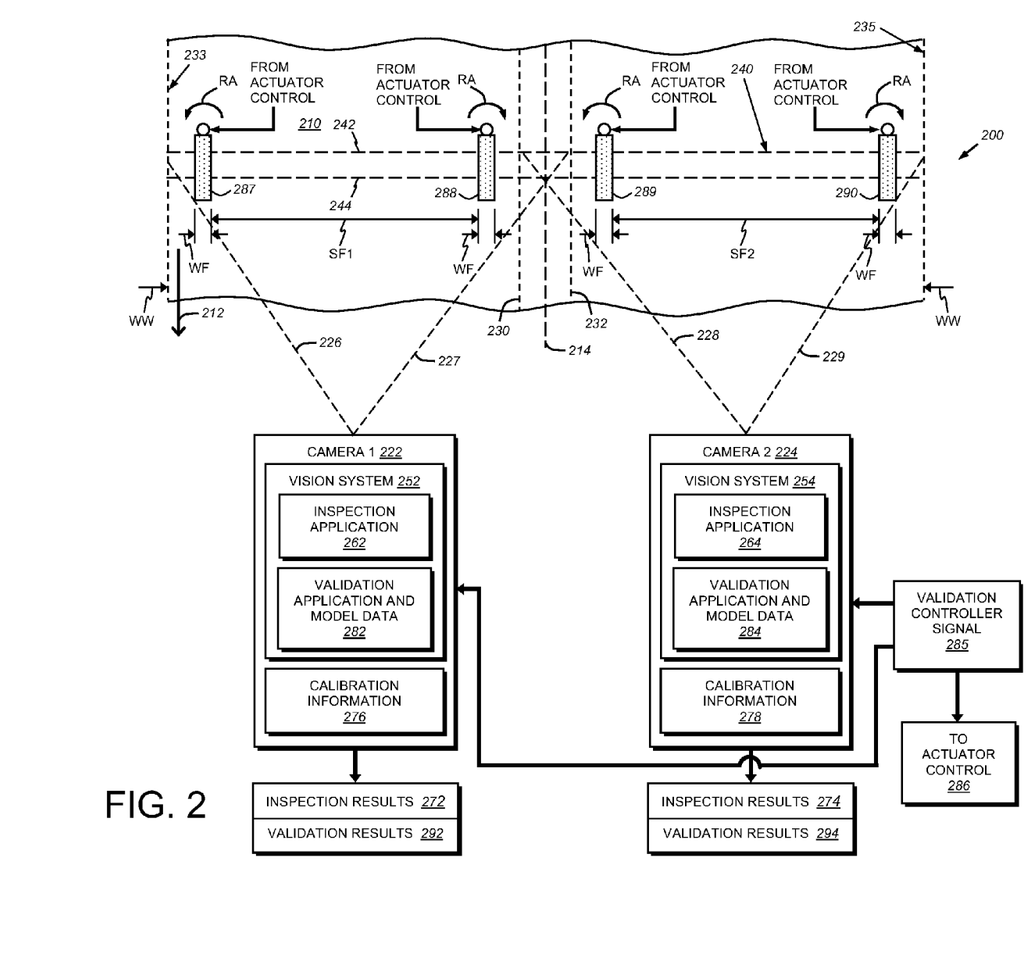
FIG. 2 is a schematic view of a multi-camera, cross-web inspection system including calibration validation according to an illustrative embodiment.

A cross-web inspection system 200 is shown in schematically in FIG. 2. While the illustrative embodiment details a web-inspection system, the principles of this description is applicable to a variety moving surface inspection systems. Such systems can employ one or more cameras, arranged to image predetermined positions along the region of interest to perform surface inspection across the width of the surface, transverse to the downstream direction of motion. As shown, the system is arranged generally similar to that shown and described in FIG. 1. It includes a web, or other moving surface 210 requiring inspection for defects. The web 210 moves downstream (arrow 212) at a predetermined rate that can be tracked by an encoder or other movement mechanism (not shown). The rate can be used to determine the frequency of the validation process in certain embodiments. Otherwise, validation occurs at a predetermined timer interval. The web 210 in this example is shown divided along its width into two sides, separated by an approximate centerline. Each web half is inspected by a discrete camera, Camera 1 (222) and Camera 2 (224). The filed of view of each camera 222 and 224 is shown by respective dashed lines 226, 227 and 228, 229. As shown, the fields of view extend to opposite widthwise boundaries (dashed lines 233, 235) of the region of interest. The fields of view likewise overlap in the central region between web halves (see crossing dashed lines 227 and 228). The exemplary overlap region is thus defined by dashed lines 230, 232. The amount of overlap is highly variable. It should be sufficient to ensure complete imaging of the entire web 210 where appropriate. The region of interest 240 is bounded by dashed lines 242 and 244 and spans across the width of the web 210. This region of interest corresponds generally with the dimensions of the light strip of the underlying illumination bar, described further below. In general a strip of LED light sources, which can be covered by a diffuser window, generates the illumination in an illustrative embodiment. Other illumination arrangements, including those using other types of light sources, can be employed in alternate embodiments. In general, the region of interest is the area within the field of view that the inspection system analyzes for defects.

The cameras 222 and 224 can be any acceptable vision system camera including those employing a two-dimensional pixel array and those employing a one-dimensional, line-scan array. The illustrative vision system cameras 222, 224 each include a respective vision processor 252, 254 that runs an inspection application 262, 264. The inspection application 262, 264 can operate any appropriate vision system tasks and/tools used to inspect a surface for defects. The application can include appropriate model information, which is compared to acquired images of the web to determine if a defect is present. The results 272, 274 of the inspection process can be stored in an inspection file as described above. These results can be appended to a production run (for example a web roll) as a quality control measure. The results can also be used to operate specific line processes, such as an alert or a line stoppage command. In alternate embodiments, it is expressly contemplated that the camera(s) can be interconnected with a discrete vision system processor (not shown) that processes images acquired by the camera(s), and generates inspection results.

The vision processor can include stored model data (not shown) provided from an initial training procedure. Likewise, each camera 222, 224 can include respective calibration information 276, 278. This data can include information about camera-specific intrinsic and extrinsic parameters, as well as focus and alignment data, among other parameters. This data is set at calibration time, before runtime operation begins.

Notably, the vision processor 252, 254 in each camera includes a calibration and alignment validation application and model data related to the validation procedure 282, 284, respectively. The validation application 282, 284 operates in response to a validation controller 285, which can be a discrete hardware component or a part of the camera(s), and can include an onboard timer or interface with a line encoder (or other trigger mechanism) so as to periodically run the validation application during system runtime operation. The validation controller also interfaces with an actuator control 286, that operates each of a plurality of actuable flags or targets 287, 288, 289 and 290 that selectively move into and out of the region of interest 240 so as to occlude the light of the illumination bar along a predetermined portion of the overall width WW of the region of interest 240. The deployed position for the flags 287, 288, 289 and 290 is shown in FIG. 2. In that deployed position each flag generates an occluded block along the light strip. The occluded block is defined by the width WF of the flag. The widths can be identical or can vary for each flag. The flags in each web half are separated by a respective distance SF1 and SF2 that is also known. As described further below, the flags can be opaque, translucent and/or include a partially opaque or translucent pattern. At least one flag is provided within each camera's field of view, although in this embodiment, a plurality of flags (at least two) are located in the field of view of each camera 222, 224.

Note that the various controls and controllers herein can be implemented as separate devices, such as a programmable logic controller (PLC). Control functions can be combined into one or more hardware devices executing appropriate computer readable program instructions. Various functions and processes described with respect to the control or controllers can be instantiated in the vision system applications where appropriate.

Figure 3:
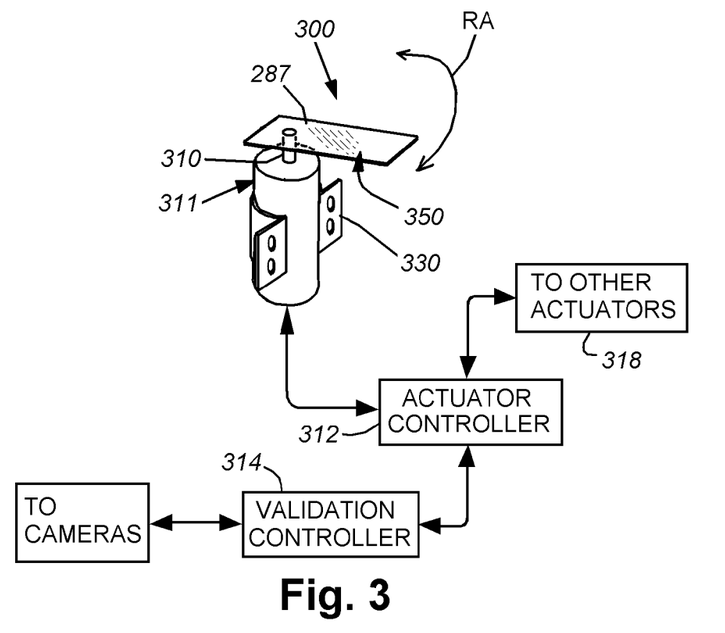
FIG. 3 is a diagram of an illustrative flag assembly including a rotary actuator and mounting bracket, showing interconnection to other control components of the system.
Figure 4:
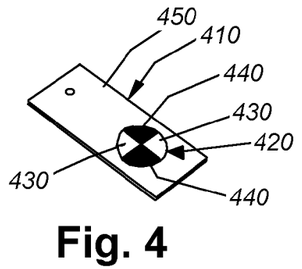
FIG. 4 is a perspective view of a flag according to an alternate embodiment, including an illustrative fiducial having differing regions of light transmissivity.
Figure 5:
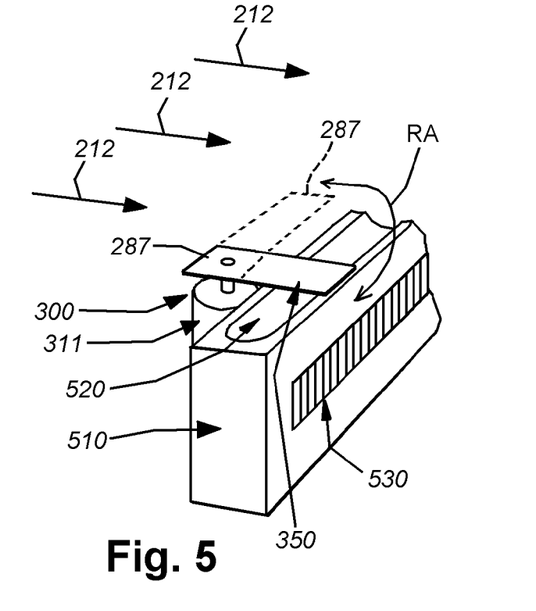
FIG. 5 is a perspective view of a portion of a light bar illuminator for use in the system of FIG. 2 including one of a plurality of exemplary flag assemblies positioned at predetermined positions along the light bar.

The validation application 282, 284, can be part of the overall inspection application, although it is shown herein separately for illustrative purposes. Like inspection, validation can be carried out in each camera or can be carried out by one or more discrete, interconnected processors that receive acquired image data from the camera arrangement. With further reference to FIGS. 3, 4 and 5, a flag actuation assembly 300 is shown in greater detail. The depicted assembly 300 rotates the illustrative flag 287 through and arc (curved double-arrow RA) that is at least 90 degrees. This allows the flag to move fully into and out of the light strip. In an embodiment, the flag is secured to an axle 310, which is driven by a rotary actuator 311 that comprises a conventional rotary solenoid operated by an electric control signal. The signal is issued by an appropriate actuator controller 312, which can be of a conventional design. The controller also operates the other actuators (represented by block 318) at an appropriate time—typically simultaneously. The actuator controller receives a control signal (285 in FIG. 2), as described above, at periodic intervals from the validation controller 314. The actuator body is provided with an appropriate mounting bracket 330 that allows mounting on a fixed surface with respect to the inspection surface and cameras.

In an illustrative embodiment, and with particular reference to FIG. 5, the actuators can be mounted on the illumination bar 510, residing under the moving surface to project light therethrough for receipt at the overlying cameras. The downstream motion of the overlying web/surface is represented by the arrows 212. The exemplary actuator assembly 300 is representative of all actuators mounted across the bar 510. As shown the actuator moves the flag 287 to the depicted deployed position (shown in solid lines) from an undeployed position (shown in phantom). In the undeployed position, the flag 287 leaves the light strip 520 free of obstruction, while the deployed position occludes a portion of the overall length (in a widthwise web direction) of the strip as shown. This creates a shadow on the projected illumination in the region of interest that is readily detected by the cameras during the validation procedure. The outline shape of the flag is highly variable. In an illustrative embodiment, the actuator(s) are mounted on the illumination bar 510 on the upstream side. The actuators can be alternatively mounted on the downstream side. The actuators operate at a high speed. A complete deploy-undeploy cycle can be completed in approximately 1-2 milliseconds.

The depicted light bar includes an optional rule-marking 530 (FIG. 5), which can be used during setup and camera calibration to determine the location of each flag, as well as other items within the scene. Camera setup, alignment and calibration are accomplished according to conventional techniques. Such techniques can employ laser optics to pinpoint the field of view of each camera and ensure proper overlap, and also generally ensure proper alignment of each camera with respect to the other camera.

In general, the illustrative validation procedure compares the location of each flag, and its relative size in the region of interest against the expected configuration, including the flag's orientation, position, size, and (optionally) intensity for the flags based upon a model created at training time. The model can be an actual image of the deployed flags or can be a synthetic model based on known sizes, locations and distances for flags relative to the region of interest. Validation can check on camera alignment and overlap based upon the detected position and size of each flag. It can also check focus, and whether a camera has moved closer or further away than the calibrated distance, based on the size of each flag. Validation can also check whether illumination intensity has changes. In an illustrative embodiment, this can be accomplished by providing at least part of the flag surface 350 with a translucent (partial-light-blocking) material. By way of example, the use of an 80-percent light-blocking material can be used. This allows for the transmission of a significantly reduced, and discrete, level of illumination in the outline of a flag. The reduced level of light defines an intensity value in the validation procedure recognizes as a baseline illumination level. Any variation from this level can be used to indicate a change in illumination intensity. The measured intensity can also be used to determine a variation in the thickness or density of the surface through which the light is transmitted.

Alternatively, as shown in FIG. 4, an exemplary flag 410 can include a pattern or other fiducial 420 that consists of transparent and translucent segments 430, 440 that are surrounded by an opaque surface 450. It is expressly contemplated that a variety of combinations of transparent, translucent and opaque patterns can be combined on a surface to create a flag according to an illustrative embodiment. Such a pattern can allow the validation procedure to determine illumination intensity as well as a variety of other calibration parameters.

Figure 6:
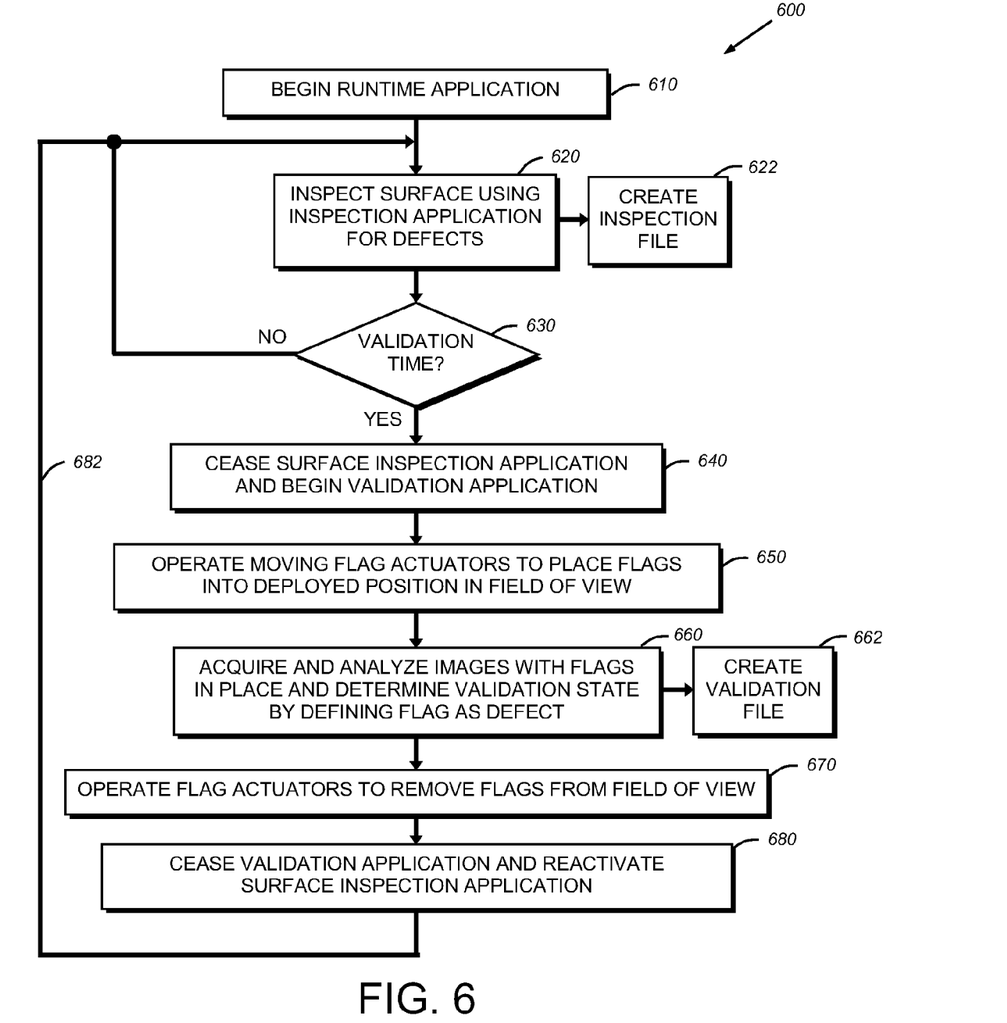
FIG. 6 is a flow diagram of a runtime surface inspection and camera calibration validation procedure implemented in the system of FIG. 2.

FIG. 6 details an illustrative procedure 600 for runtime validation of system calibration in a cross-surface (cross-web) multi-camera inspection arrangement. After calibration and training, the system begins runtime operation 610. The system inspects the moving surface using the inspection application (262 in FIG. 2) to determine the presence of defects. The results of inspection are generated and can be provided to an inspection file (step 622) associated with the production run. At a predetermined time, the validation control issues a signal (285 in FIG. 2) and the vision system operates the validation procedure (step 640 via decision step 630). At this time, the runtime cross-surface inspection procedure ceases operation. The validation controller (314 in FIG. 3) operates the actuation of the flags into a deployed position (step 650). The validation procedure can be a discrete inspection operation using the inspection application. The model data treats the flags as defects in the in the inspection application. In step 660, the cameras acquire and process images containing the flags. The vision system application compares the locations and sizes of the flags, and optionally the transmitted intensity of the flag. The flags are placed in the field of view momentarily (1-2 milliseconds for example). The validation controller then deactivates actuation (step 670) and the validation application ceases, with runtime inspection again initiating (step 680 and return branch 682). The frequency of the validation cycle is highly variable, for example, once every 10 seconds, once every 30 seconds, once per minute, etc.). During the validation cycle the validation results (292, 294 in FIG. 2), like the inspection results, can be provided to a validation file (step 662). The files can be associated with a production run, such as a web roll. The provision of a validation file to each item produced allows for enhanced quality control which includes both information relating to any defects in the item, but also realtime information as to whether the inspection system is functioning within parameters.

Figures 7, 8:
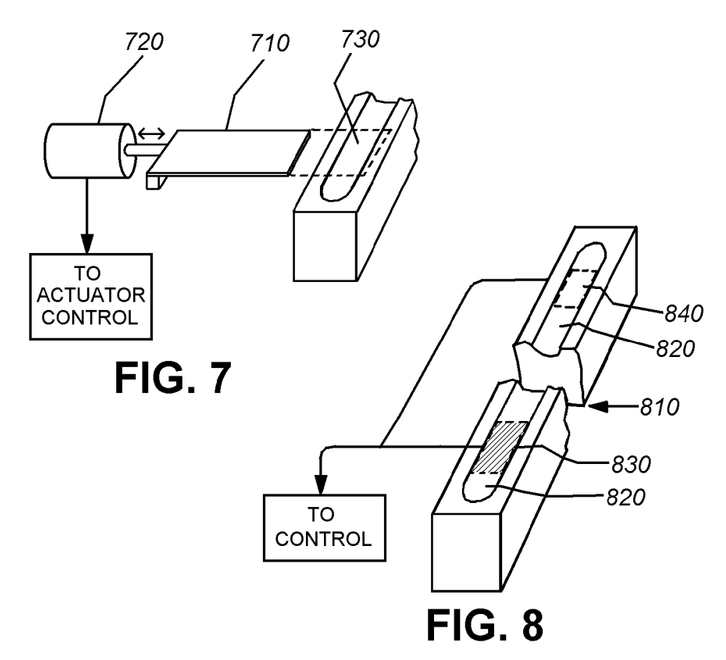
FIG. 7 is a partial perspective view of a flag and linear flag actuator positioned with respect to a portion of the light bar according to an alternate embodiment.
FIG. 8 is a partial perspective view of a light bar according to an alternate embodiment including a solid state flag formed within or overlying the diffuser window of the illumination strip.

It is expressly contemplated the technique by which flags are placed (actuated) into the region of interest is highly variable. FIG. 7 details an alternate embodiment in which one or more flags are actuated by passing them linearly (rather than rotatably) into the field of view. In this embodiment, the flag 710 is actuate linearly by a linear actuator (a solenoid for example) 720. The flag 710 moves into an occluding position with respect to the light bar's light strip window 730 (shown in phantom) when the actuator 720 strokes in a predetermined direction. The flag 710 is moved out of an occluding position with respect to the light strip window 730 when the actuator 720 strokes in an opposing direction with respect to the light strip window 730. In other embodiments, flags can be relatively thin and twist between an on-edge position with flat surface perpendicular to the light, and a deployed position with the flat surface parallel to the plane of the light window. The flags may be sufficiently thin to avoid occluding the light.

In other embodiments, the flags can be constructed from solid stare and/or semiconductor components, using, for example, an LCD curtain of predetermined size and shape positioned over predetermined sections of the illuminator. FIG. 8 details a light bar 810 in broken perspective view, showing opposing ends thereof. The light strip window 820 includes an integrated section that includes an LCD array 830, 840. When deenergized, the LCD window section allows full or nearly full transmission of light therethrough (window section 840). When energized, the window section becomes opaque, translucent (for example, by energizing a tessellating checkerboard of pixels), or patterned with opaque and transparent portions (window 830). For illustrative purposes, both a deenergized and energized window are shown together on a single strip. In a typical embodiment, all windows are energized and deenergized together, although altering the timing of each flags actuation can have advantages in certain alternate embodiments and is expressly contemplated. The flag section(s) can be constructed unitarily or integrally with the surrounding strip window 820 using conventional techniques. Alternatively, the flag window can be a separate assembly that overlies or underlies the main strip window 820.

It should be clear that the above-described system for cross-surface inspection provides a straightforward and cost-effective arrangement for validating calibration and key parameters. The system can be implemented using conventional components and existing machine vision system applications without substantial modification to hardware or software applications residing therein. The validation cycle is sufficiently short, that minimal inspection information is lost during the cycle. Desirably, the vision system can employ the same inspection application for both runtime inspection and validation without the need for additional hardware and/or software systems.

The foregoing has been a detailed description of illustrative embodiments of the invention. Various modifications and additions can be made without departing from the spirit and scope of this invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. The term "flag" or "target" and "actuation" should, thus, be taken broadly to define a variety of structures and techniques for occluding or dimming an area of an illumination strip in a region of interest. Moreover, while two cameras are employed in this illustrative embodiment, the principles herein can be applied to three or more cameras arranged across a surface to be inspected. Additionally, while the light bar in this embodiment extends in a widthwise orientation that is perpendicular to surface movement, it is expressly contemplated that the illumination and associated region of interest can extend, at a non-perpendicular angle with respect to the downstream direction of movement. In addition, while the validation procedure occurs automatically, at predetermined intervals, it is expressly contemplated that the procedure can be initiated by a user, via an appropriate user interface. Also, it is expressly contemplated that the procedures and methods described herein can be implemented in hardware, software consisting of a computer readable medium including program instructions, or a combination of hardware and software. Accordingly, this description is meant to be taken only by way of example, and not to otherwise limit the scope of this invention.

What is claimed is:

1. A system for calibrating a plurality of vision system cameras arranged to provide cross-surface inspection results comprising:
   an illumination strip extending across a moving surface that provides a region of interest with respect to the moving surface for image acquisition by each of the plurality of vision system cameras;
   a runtime surface inspection application associated with each of the vision system cameras that provides the inspection results;
   at least two flags within a field of view of each of the vision system cameras that are actuable to occlude a portion the illumination strip at predetermined times; and
   a validation application that directs the at least two flags in each field of view of each vision system camera to actuate into the region of interest and that validates at least one vision system camera setting based on acquired images of each of the at least two actuated flags with respect to an expected configuration of each of the at least two actuated flags.

2. The system as set forth in claim 1 wherein the expected configuration is based upon stored model data relating to at least one of an orientation, location, size and intensity of the at least one flag.

3. The system as set forth in claim 1 further comprising a validation controller, that directs the validation application to start and a runtime surface inspection application to cease, and to actuate the at least one flag.

4. The system as set forth in claim 1 wherein the surface inspection application includes the validation application, and the expected configuration is a set of model data provided to the surface inspection application to provide validation results.

5. The system as set forth in claim 4 wherein the inspection results and the validation results are each provided in a respective file.

6. The system as set forth in claim 5 wherein each file is associated with a predetermined production run.

7. The system as set forth in claim 1 wherein each flag is mounted on a rotary actuator.

8. The system as set forth in claim 7 wherein the actuator is mounted on the illumination strip on a side of the surface opposite a side facing the plurality of vision system cameras.

9. The system as set forth in claim 1 wherein the at least one flag includes a surface that is at least part translucent so as to provide reduced transmission of light from the illumination strip and wherein the validation application detects variations in the reduced transmission of light.

10. The system as set forth in claim 1 wherein the flag comprises at least one of a rotationally actuated structure, a linearly actuated structure and a solid state assembly that occludes a portion of the illumination strip.

11. The system of claim 1, wherein at least one of the two flags is placed within the field of view for not more than 2 milliseconds.

12. The system of claim 1, wherein at least one of the two flags comprises a translucent material.

13. The system of claim 1, wherein the at least one flag comprises at a pattern of translucent segments and transparent segments, the pattern of translucent segments and transparent segments being surrounded by an opaque surface.

14. A method for calibrating a plurality of vision system cameras arranged to provide cross-surface inspection results comprising the steps of:
   illuminating a region of interest that extends across a moving surface;
   acquiring runtime images with each of the plurality of vision system cameras;
   performing surface inspection with respect to each of the vision system cameras, so as to provide the inspection results;
   actuating, into the region of interest, at least two flags within a field of view of each of the vision system cameras to occlude a portion the illuminated region of interest at predetermined times; and
   directing the actuating of the at least two flags in each field of view of each vision system camera and then validating at least one vision system camera setting based on acquired images of each of the at least two actuated flags with respect to an expected configuration of each of the at least two actuated flags.

15. The method as set forth in claim 14 wherein the expected configuration is based upon stored model data relating to at least one of an orientation, location, size and intensity of the at least two flags.

16. The method as set forth in claim 14 further comprising providing a validation controller, that causes the step of validating to start and the step of performing surface inspection to cease, and causes the step of actuating to occur.

17. The method as set forth in claim 14 wherein the expected configuration is a set of model data provided to the step of performing surface inspection to provide validation results.

18. The method as set forth in claim 17 further comprising providing each of the inspection results and the validation results to a respective file.

19. The method as set forth in claim 18 further comprising associating each file with a predetermined production run.

20. The method as set forth in claim 14 wherein the step of actuating includes at least one of (a) moving the at least two flags rotationally, (b) moving the at least two flags linearly and (c) operating a solid state section that's selectively occludes light.

21. The method as set forth in claim 19 further comprising operating the actuator to move the flags into a position that blocks a portion of an illumination strip with respect to a side of the surface opposite a side facing the plurality of vision system cameras.

22. The method as set forth in claim 14 further comprising providing a surface to the at least two flags that is at least part translucent so as to provide reduced transmission of light from an illumination strip and detecting variations in the reduced transmission of light.

23. A system for calibrating a plurality of vision system cameras arranged to provide cross-surface inspection results comprising:
   an illumination strip extending across a moving surface that provides a region of interest with respect to the moving surface for image acquisition by each of the plurality of vision system cameras;
   a runtime surface inspection application associated with each of the vision system cameras that provides the inspection results;
   at least one flag within a field of view of each of the vision system cameras that is actuable to occlude a portion the illumination strip at predetermined times, wherein the at least one flag is placed within the field of view for not more than 2 milliseconds; and a validation application that directs the at least one flag in each field of view of each vision system camera to actuate into the region of interest and that validates acquired images of each at least one actuated flag with respect to an expected configuration of each at least one actuated flag.

* * * * *